United States Patent
Curtin et al.

[11] Patent Number: 6,028,017
[45] Date of Patent: Feb. 22, 2000

[54] HIGH STRETCH BREATHABLE NONWOVEN TEXTILE COMPOSITE

[75] Inventors: Patrick J. Curtin, Greenville, N.C.; Victor S. Day, Portsmouth; William E. Russell, Middletown, both of R.I.

[73] Assignee: The Moore Company, Westerly, R.I.

[21] Appl. No.: 09/045,487

[22] Filed: Mar. 20, 1998

Related U.S. Application Data

[60] Provisional application No. 60/041,159, Mar. 20, 1997.

[51] Int. Cl.$^7$ ................... D04H 5/18; D04H 5/24
[52] U.S. Cl. ............ 442/370; 442/374; 428/86; 428/131; 428/137; 428/138; 428/304.4; 428/309.9
[58] Field of Search ............... 442/370, 374; 428/86, 131, 137, 138, 304.4, 309.9

[56] References Cited

U.S. PATENT DOCUMENTS

| | | | |
|---|---|---|---|
| 2,805,182 | 9/1957 | Hallenbeck | 154/48 |
| 3,080,255 | 3/1963 | Winkelmann | 117/47 |
| 3,098,755 | 7/1963 | Barth et al. | 117/33 |
| 3,312,584 | 4/1967 | Charlton et al. | 161/81 |
| 3,382,138 | 5/1968 | Barth | 161/190 |
| 3,528,878 | 9/1970 | Lubowitz et al. | 161/188 |
| 3,547,764 | 12/1970 | van Amerongen | 161/184 |
| 4,102,808 | 7/1978 | Straka | 252/354 |
| 4,446,189 | 5/1984 | Romanek | 428/152 |
| 4,652,487 | 3/1987 | Morman | 428/138 |
| 4,655,760 | 4/1987 | Morman et al. | 604/385 |
| 4,657,802 | 4/1987 | Morman | 428/152 |
| 4,761,324 | 8/1988 | Rautenberg et al. | 428/198 |
| 4,846,164 | 7/1989 | Martz | 128/155 |
| 4,879,170 | 11/1989 | Radwanski et al. | 428/233 |
| 5,336,545 | 8/1994 | Morman | 428/152 |
| 5,336,554 | 8/1994 | Knight | 428/230 |
| 5,529,830 | 6/1996 | Dutta et al. | 428/176 |
| 5,540,976 | 7/1996 | Shawyer et al. | 428/198 |
| 5,592,690 | 1/1997 | Wu | 2/67 |
| 5,607,798 | 3/1997 | Kobylivker et al. | 442/381 |
| 5,683,787 | 11/1997 | Boich et al. | 428/198 |

FOREIGN PATENT DOCUMENTS

| | | | |
|---|---|---|---|
| 0411236 | 2/1991 | European Pat. Off. | C08L 75/04 |

*Primary Examiner*—Terrel Morris
*Assistant Examiner*—Ula C. Ruddock
*Attorney, Agent, or Firm*—Darby & Darby

[57] ABSTRACT

A composite nonwoven fabric is constructed to have high breathability, a low modulus and a good hand. The composite is comprised of a fibrous nonwoven material attached to a highly elastic breathable foam film substrate. The foam film substrate is dimensioned to be thin enough to provide numerous apertures and/or voids therethrough. The attachment of the fibrous nonwoven material to the foam film substrate is accomplished by needlepunching portions of at least some strands of the nonwoven material through the apertures in the elastic foam film. During the needlepunching process, the numerous apertures and/or voids in the foam film facilitate the passage of strands of the nonwoven material through the foam film by the needles while minimizing damage to the structure of the foam film by the needles. Alternatively, the composite nonwoven textile is constructed by attaching fibers to the breathable elastic foam film by flocking. The fibers may be attached by an adhesive or may be attached by application to the elastic foam film while the film is still "wet" (i.e. before the film is cured).

14 Claims, No Drawings

6,028,017

HIGH STRETCH BREATHABLE NONWOVEN TEXTILE COMPOSITE

This application is based upon the Provisional Patent Application Serial No. 60/041,159 filed on Mar. 20, 1997, which is incorporated herein by reference, and Applicants claim the benefit of the filing date of the aforesaid provisional application under 35 U.S.C. §119.

FIELD OF THE INVENTION

The present invention relates to the production of novel elastic nonwoven textiles with a fabric-like feel for use in a wide range of applications, such as, for example, garments, diapers, personal care products and medical care products.

In the garment and diaper industries, for example, elastic textiles used for form fitting articles have a unique set of requirements. These requirements include a low stretch modulus, high dimensional stability (to retain the article's shape), low permanent set (to avoid losing the snug fit of a garment or diaper), and tear resistance (to avoid tearing while being punctured by the sewing needle). Elasticity, the ability of the textile to be stretched and then return to approximately its original size, is highly desirable in many applications. Other highly desirable characteristics, particularly in garments and personal care articles, are: water repellence, the ability of a textile to retain fluid within an article such as a diaper, or shed fluid outside of an article such as outdoor apparel (e.g. socks, gloves, hats, pants, shirts, jackets and the like); breathability, the ability of a textile to ventilate a confined space (e.g. to allow an exchange of vapors through the textile); softness (e.g. "hand" and "drape"), the tactile and visual aesthetics of a textile, such as, for example, the fabric-like feel of a textile when it contacts the skin of a user; and economy of manufacture, so that low cost single use or limited use articles may be marketed to the consumer.

Stretchable nonwoven fabrics have been produced, but the known composite nonwoven materials which have, to date, been marketed have been deficient in one or more of the desirable characteristics. Breathable elastic nonwoven textiles have heretofore generally been composites or laminates constructed on either a breathable fibrous substrate web or a non-breathable film substrate web, the latter being processed separately, generally by mechanical means, to be breathable. With respect to textiles constructed on the fibrous substrate web, the cost tends to be higher because of the complex processes required to create the fibrous substrate. With respect to textiles constructed on the film substrate web, initial cost of the film substrate is substantially lower than similarly dimensioned fibrous substrates, but additional processing of the film to provide breathability increases the ultimate cost of the product and may reduce the strength of the film by physically damaging the film structure. The known composite elastic nonwoven textiles have not been formed by utilization of the novel and economical construction and processes of the present invention.

All of the patents and publications referenced below, and the contents of those patents and publications, are incorporated herein by reference.

For example, U.S. Pat. No. 4,657,802 to Mormon discloses a method for making a cloth-like breathable textile based on a fibrous elastic nonwoven web. While the fibrous elastic nonwoven web is held in a stretched condition, a fibrous gatherable nonwoven web is attached to the stretched fibrous elastic web by any of a variety of attachment methods, such as heat bonding (melt blowing), sonic bonding, entanglement (spin bonding), or adhesion (e.g. fibrous gatherable web applied directly to a tacky fibrous elastic web). When the fibrous elastic web is released from the stretched condition and allowed to relax, the fibrous gatherable web is gathered to form a soft surface layer on the textile. A second layer of fibrous gatherable web may be applied to the opposite side of the fibrous elastic web if desired. Where the fibrous gatherable web is adhered to one side of a tacky fibrous elastic web, the second layer of fibrous gatherable web on the opposite side of the tacky fibrous elastic web may be required for purposes of post manufacturing handling, processing and/or shipping.

U.S. Pat. No. 4,879,170 to Radwanski et al. discloses a nonwoven fibrous elastomeric material, including absorbent webs and fabric web material, and methods of making the same. The elastomeric material is a hydro-entangled conform (e.g. admixture) of meltblown fibers and fibrous material (for example, meltblown fibers of an elastomeric material and at least one of (1) pulp fibers, (2) staple fibers, (3) meltblown fibers and (4) continuous filaments), with or without particulate material. The fibrous elastomeric nonwoven web material may be attached to a film or fibrous web.

U.S. Pat. No. 4,446,189 to Romanek discloses a nonwoven textile fabric laminate having at least one layer of nonwoven textile attached to an elastomeric film by needlepunching. The nonwoven textile is attached to the elastomeric film while the film is held in a stretched condition. Upon release of the elastomeric film from the stretched condition, the nonwoven textile exhibits increased bulk. In order to provide a soft, fabric-like feel to both sides of the elastomeric substrate, a layer of nonwoven textile must be attached to each side of the elastomeric substrate.

While the above-discussed documents disclose products and processes which exhibit some of the characteristics or method steps of the present invention, none discloses or suggests the presently claimed process or product resulting from this process, and none achieves the advantages of the present invention. The nonwoven textiles produced according to the teachings of U.S. Pat. Nos. 4,657,802 and 4,879,170 require a fibrous nonwoven elastomeric web as a substrate. The production of fibrous nonwoven elastomeric web substrates requires relatively complex manufacturing processes and is therefore relatively more expensive than, for example, production of a continuous elastomeric film. The nonwoven textile produced according to the teachings of U.S. Pat. No. 4,446,189 requires attachment of fibrous nonwoven textile to both sides of an elastomeric film substrate to achieve a cloth-like feel on both sides of the laminate textile. Textiles produced by applying flocked fibers to an elastic film, in addition to requiring application of the fibers to both sides of the film, require perforation of the film, in a pre- or post-flocking operation, to achieve breathability. cl OBJECTS OF THE INVENTION Thus, there has been a desire in the area of garment and diaper fabrication to provide a textile which is (1) highly elastic over its entire surface—to provide a tight yet comfortable fit; (2) selectively water repellent (i.e. impermeable), absorbent, or water transferable (permeable)—to retain fluid materials within or to shed fluid outside the confines of the garment or diaper, to absorb water or to transfer water, respectively, according to the application requirements; (3) breathable (i.e. vapor permeable)—to allow an exchange of vapors through the textile; (4) soft on both sides of the substrate—for improved comfort, and (5) inexpensive to manufacture—so that articles manufactured from the textile may be economically marketed to the consumer.

The present invention overcomes the disadvantages of the known composite nonwoven textiles by providing a novel composite nonwoven textile which is highly elastic, water repellant (or alternatively, absorbent or water transferable), breathable, soft and inexpensive to manufacture.

Accordingly, it is an object of the present invention to provide a new composite nonwoven textile which is composed of a breathable high-elastic foam film having fibrous nonwoven web joined thereto.

Another object of the present invention is to provide a composite nonwoven textile which is composed of a breathable high-elastic foam film having non-elastic fibrous nonwoven web material joined thereto, wherein the non-elastic fibrous nonwoven web material is made elongatable by mechanical working (e.g. needlepunching).

Another object of the present invention is to provide a highly elastic, breathable, soft, composite nonwoven textile by a process which requires fewer, less complicated manufacturing steps.

Another object of the present invention is to provide a highly elastic, breathable, composite nonwoven textile with a soft surface on opposite sides of the material in a single processing step by passing fibers of a nonwoven textile partially through apertures and/or voids in an elastic foam film substrate, so that portions of the fibers extend away from the foam film on opposite sides of the film substrate.

Another object of the present invention is to provide a composite nonwoven textile which has a degree of breathability substantially determined by the degree of breathability of the substrate film before the nonwoven textile is joined thereto.

SUMMARY OF THE INVENTION

In accordance with the present invention, a composite nonwoven textile is constructed by attaching a fibrous nonwoven material to a highly elastic breathable foam film. In the preferred embodiment, the foam film is dimensioned to be thin enough to provide numerous apertures and/or voids therethrough. The attachment is preferably accomplished by needlepunching the nonwoven textile to the elastic foam film. During the needlepunching process, the numerous apertures and/or voids in the foam film accommodate the passage of strands of nonwoven textile through the foam film by the needles while minimizing damage to the structure of the foam film by the needles.

In a second embodiment of the present invention, a composite nonwoven textile having high breathability, a low mudulus (e.g., elongation greater than 200% but preferably in a range from 200–800%) and a good hand is constructed by attaching fibers to the breathable elastic foam film by flocking. The fibers may be attached by an adhesive or may be attached by application to the elastic foam film while the film is still "wet" (i.e. before the film is cured).

In a third embodiment of the present invention, a composite nonwoven textile is constructed by attaching a nonwoven textile to an elastomeric film substrate, the elastomeric film substrate having a high breathability, a low modulus (e.g., elongation greater than 600% but preferably in a range from 600–1200%) and a good hand.

DETAILED DESCRIPTION OF THE INVENTION

The terms "elastic" and "elastomeric" are used interchangeably herein to mean any material which, upon application of a biasing force, is stretchable to a stretched, biased length which is at least about 125 percent, that is about one and one quarter, of its relaxed, unbiased length, and which will recover at least about 40 percent of its elongation upon release of the stretching, elongating force. A hypothetical example which would satisfy this definition of an elastomeric material would be a one (1) inch sample of a material which is elongatable to at least 1.25 inches and which, upon being elongated to 1.25 inches and released will recover to a length of not more than 1.15 inches. Many elastic materials may be stretched by much more than 25 percent of their relaxed length and many of these will recover to substantially their original relaxed length upon release of the stretching, elongating force and this latter class of materials is generally preferred for purposes of the present invention. The preferred substrate material is capable of stretching more than 600%, and preferably in a range from 600–1,200% of its relaxed length, and upon release of the stretching, elongating force recovers to substantially its original relaxed length.

As used herein the term "recover" refers to a contraction of a stretched material upon termination of a biasing force following stretching of the material by application of the biasing force. For example, if a material having a relaxed, unbiased length of one (1) inch was elongated 100 percent by stretching to a length of two (2) inches the material would have a stretched length that is 200 percent of its relaxed length. If this exemplary stretched material is contracted, that is, is recovered, to a length of one and five tenths (1.5) inches, after release of the biasing and stretching force, the material would have recovered 50 percent (0.5 inch) of its elongation.

As used herein the terms "nonelastic" or "nonelastomeric" refer to and include any material which is not encompassed by the terms "elastic" or "elastomeric."

As used herein the term "meltblown micro fibers" refers to small diameter fibers having an average diameter not greater than about 100 microns, preferably having a diameter of from about 0.5 microns to about 50 microns, more preferably having an average diameter of from about 4 microns to about 40 microns and which are made by extruding a molten thermoplastic material through a plurality of fine, usually circular, die capillaries as molten threads or filaments into a high velocity gas (e.g. air) stream which attenuates the filaments of molten thermoplastic material to reduce their diameter to the range stated above. Thereafter, the meltblown micro fibers are carried by the high velocity gas stream and are deposited on a collecting surface to form a web of randomly disbursed meltblown micro fibers. Such a process is disclosed, for example, in U.S. Pat. No. 3,849,241 to Butin and the disclosure of this patent is hereby incorporated by reference.

As used herein the term "spunbonded micro fibers" refers to small diameter fibers having a diameter not greater than about 100 microns, preferably having a diameter of from about 10 microns to about 50 microns, more preferably having a diameter of from about 12 microns to about 30 microns and which are by extruding a molten thermoplastic material as filaments through a plurality of fine, usually circular, capillaries of a spinnerette with the diameter of the extruded filaments then being rapidly reduced as by, for example, educative drawing or other well known spunbonding mechanisms. The production of spunbonded nonwoven webs is illustrated in U.S. Pat. No. 4,340,563 to Appel and the disclosure of this patent is hereby incorporated by reference.

As used herein the terms "nonwoven textile" and "nonwoven fabric" are used interchangeably, and include any textile material which has been formed without use of textile weaving processes which produce a structure of individual fibers which are interwoven in an identifiable repeating manner. The fibers or threads of a "nonwoven" are interlaid, but not in a regular, repetitive manner as in a knitted fabric. Specific examples of nonwoven textiles or fabrics would include, without limitation, a meltblown nonwoven web, a spunbonded nonwoven web, an apertured film, a microporous web or a carded web of staple fibers.

As used herein the term "consisting essentially of" does not exclude the presence of additional materials which do not significantly affect the properties and characteristics of a given composition. Exemplary materials of this sort would include, pigments, anti-oxidants, stabilizers, surfactants, waxes, flow promoters, solid solvents, particulates and materials added to enhance processability of the composition.

As used herein, the term "garment" means any type of apparel which may be worn. This includes industrial work wear and coveralls, undergarments, pants, shirts, jackets, gloves, socks, and the like.

As used herein, the term "medical product" means surgical gowns and drapes, face marks, head coverings, shoe coverings wound dressings, bandages, sterilization wraps, and the like for medical, dental or veterinary applications.

As used herein, the term "personal care product" means wipes, diapers, training pants, absorbent underpants, adult incontinence products, and feminine hygiene products.

According to the present invention, a composite textile is constructed by attaching a fibrous nonwoven textile web or loose fiber material to an apertured elastomeric film substrate web by needlepunching, flocking, wet adhering, or other known attachment techniques. The resulting composite textile will be stretchable (i.e. elongatable) more than 200%, but preferably in a range from 200% to 800%, of its relaxed unbiased length, and upon release of the stretching will recover in a range from 80% to 90% of its elongation (i.e. have a permanent set of 20% or less). The composite textile will have excellent breathability due to the apertured structure of the film substrate. Also because of apertured structure of the film substrate, damage to the film substrate due to the preferred attachment method, needlepunching, is minimized, thus resulting in a reduced loss of substrate strength.

The fibers and nonwoven textile of this invention can include, for example, spunbond fabric, meltblown fabric, staple fibers, glass fibers, paper and other commonly used or commercially available materials known to those skilled in the art. The nonwoven textile is preferably a spunbond or meltblown fabric with suitable qualities for providing a soft, fabric-like feel. The nonwoven component may be an elastic or nonelastic ("rigid") fabric, with oriented or random fibers. A suitable nonelastic nonwoven fabric, for example, is a nonwoven thermal bonded or spunbonded hydrophobic polypropylene fabric having oriented fibers and a basis weight of 22 gsm (grams per square meter). However, it will be appreciated by those skilled in the art that numerous other nonwoven fabrics are also suitable.

The preferred method of attachment, needlepunching, provides excellent entanglement of fibers of the nonwoven textile with the apertures of the film substrate. The nonwoven textile is thus firmly attached to the film substrate, and resists peeling away from the substrate. In combination with the contemplated apertured film substrate, needlepunching also provides several other advantages. First, as noted above, because the film substrate is apertured, the needlepunching attachment process is less likely to damage the film substrate, particularly if the film substrate is provided with apertures sized to receive the needles without tearing the structure of the film material forming the aperture. This benefit is further facilitated by the ability of the substrate film to stretch (e.g. elongate), for example, in a range from 600% to 1200% of its relaxed, unbiased length. A film substrate provided with suitably sized apertures and high stretch capabilities permits the needles of the needlepunching process to pass in and out of the film substrate apertures with minimum damage to the film substrate structure.

In another advantage of the needlepunching process of attachment, the needles carry portions of the fibers of the nonwoven fabric from one side of the film substrate through the apertures to the opposite side of the substrate. When the needles are withdrawn from the substrate, fibers remain in the apertures, with portions extending from opposite sides of the aperture. Thus, the nonwoven fabric fibers, which in the preferred embodiment are provided in the manufacturing process line to only one side of the film substrate, are found extending from both sides of the substrate after the single step needlepunching process is completed. The resulting composite therefore has nonwoven fabric fibers on both sides of the film substrate, and has a soft, fabric-like feel on both sides of the finished product. Furthermore, the manufacturing process for providing the nonwoven fibers to both sides of the film substrate by needlepunching is simpler than other attachment processes which would require providing nonwoven material to both sides of the substrate prior to attachment to the substrate, either simultaneously at one process line location, or at subsequent process line locations, and would require at least a second attachment process.

Finally, where a nonelastic ("rigid") nonwoven fabric is selected for the composite construction, the needlepunching process has the added advantage of mechanically working the nonelastic nonwoven fabric to loosen the fibers of the fabric and make the fabric softer and more pliable. This mechanical working of the nonelastic nonwoven fabric by the needlepunching attachment process is similar in effect to the known process of ringrolling nonelastic nonwoven fabrics to achieve a fabric-like feel.

The elastomeric film substrate is a breathable, apertured film made of any number of known natural or synthetic elastomeric polymer materials, such as, for example, rubber, polyurethane, polyester, polyetherester, polyamide, polyolefin, or other like materials known in the art.

In the preferred embodiment, the film is provided with voids and apertures formed before or during curing of the film by means other than mechanical piercing or puncturing. Elastomeric films with mechanically formed voids and apertures tend to be weaker due to damage sustained to the structure surrounding each void or aperture in the mechanical void and aperture forming process. According to the present invention, the voids and apertures are formed before or during curing of the polymer film and therefore have undisturbed contiguous structure surrounding the voids and apertures, free from damage such as, for example, rips and tears associated with mechanical aperture forming processes. This undisturbed contiguous structure surrounding the voids and apertures provides additional strength and higher elasticity characteristics to the film substrate of the present invention.

In the present invention, the non-mechanically formed voids and apertures are provided to the film by processing an uncured polymer in a methods similar to those used to form polymer foams. Generally, a thickened and whipped latex emulsion is prepared to form a frothed emulsion. The frothed emulsion is cast and cured to form a cellular sheet or film. The emulsion may be whipped with a blowing agent to introduce gas to the emulsion, or the blowing agent can be a chemically generated gas such as carbon dioxide. Alternatively, the blowing agent can be air introduced mechanically to the emulsion, by frothing for example, using a mixing head. For example, U.S. Pat. No. 3,968,285 to Coffin et al. discloses the formation of a foam latex composition, prepared by mechanically whipping air into a latex emulsion, and then depositing the latex froth on a surface, and heating to effect the desired cure. Several other patents disclose similar approaches to forming elastomeric foams including U.S. Pat. No. 3,862,879 to Barron et al., U.S. Pat. No. 4,049,587 to Straka and U.S. Pat. No. 3,336,242 to Hampson et al. Various additives may be included with the emulsion, such as fillers, surfactants and thickeners, to enhance the processing or resulting product. The Kirk-Othmer Encyclopedia of Chemical Technology includes a useful review of foamed plastics (4th Ed., Vol. 11, pp. 730–783), and frothing (pp. 742–43).

In the preferred embodiment, a latex or emulsion of styrene block copolymer or a polychloroprene (CR-neoprene) polymer is prepared. Thickening agents are added to create a gel of approximately 100,000 centipoise. During the thickening stage, air or gas is introduced to the mixture by whipping (i.e., causing cavitation during mixing) or by using a microdiffuser (i.e., an air stone) to introduce a gas of uniform bubble size. After the air has been mixed into the polymer, a refining step is used to insure uniform pore size and distribution. This is done by mixing the mixture with a high shear mixer. By finishing processes known in the art of foam preparation, the pores are converted to apertures and voids in the film.

The material is then cast onto a belt to a desired thickness with a doctor blade. Water is removed by drying. Suitable thicknesses for the resultant film range from 0.001 to 0.1 inches. The resulting film has high breathability, a low modulus (greater than 600% but preferably in a range from 600–1,200% elongation) and a good hand. Furthermore, by adjusting the size of the pores in the film, the characteristics of the film can be selectively controlled. For example, providing smaller apertures enhances the water repellant characteristic of the film. Conversely, increasing the size of the apertures decreases the water repellant characteristic of the film while increasing the capability of the film to absorb or transfer water. It will thus be understood that the size, quantity and distribution of the pores and resulting apertures can be selected to provide characteristics for a particular textile application.

In another embodiment, the nonwoven high-stretch textile composite can be produced by coating the breathable elastomer film substrate web with loose fibers provided by a flocking process. The flocking process, which is well known in the art and is shown, for example in U.S. Pat. No. 3,098,755 to Barth et al., provides the advantage of producing a breathable textile composite from an economical elastomeric film substrate without the step previously required in the prior art of mechanically forming apertures in the film substrate to provide porosity. Production of the nonwoven composite textile by flocking loose fibers onto the breathable elastomer film web is an economical alternative to needlepunching nonwoven fabric onto the film. Elimination of the step previously required in the prior art of mechanically forming apertures, either in the substrate to be flocked or in the substrate after flocking, for breathability, further enhances the economy of producing the composite textile by this method. In the present invention, loose fibers may be attached to a fully cured film substrate with a suitable adhesive or other intermediate attachment means known in the art. Preferably, however, the loose fibers are provided to the film substrate before the film is fully cured, i.e. while the film substrate is still sufficiently "wet" (i.e. uncured) to allow loose fibers to adhere to the film. Subsequent curing of the film substrate firmly attaches the fibers to the substrate.

A composite textile was made according to the present invention using a commercially available polypropylene with a basis weight of 22 gsm (0.04 Lbs/SY—pounds per square yard). Additional polyester fibers were added to ensure adhesion between the nonwoven and the film. The film was a produced to have a basis weight of 0.12 Lbs/SY. A test was conducted to compare the nonwoven composite textile made according to the present invention with a sample textile taken from a commercially available diaper panel. The test showed that the sample made according to the invention compared favorably to the commercially available diaper panel.

The basis weight of each sample was determined by cutting a 1 inch by 6 inch (2.54 cm×15.24 cm) piece of each textile. Each sample was placed on a balance and weighed to the nearest 0.001 grams. The weight of each sample was multiplied by 0.4762 to obtain the basis weight in Lbs/SY (pounds per square yard) or 0.2713 to obtain the basis weight in Kg/m2 (Kilograms per square meter).

The caliper (also known as the thickness or "gauge") was measured on a dial-type thickness gauge, according to ASTM 1055–80, having a foot of 1.25 inches (3.18 cm) diameter, with 25 gram dead load pressure, and a dial indicator graduated to 0.001 inches (Federal Products #57B-1-Y7692 or similar). A sample of each textile was cut having a minimum length of 8 inches (20.32 cm) and a minimum width of 1.5 inches (3.81 cm). The sample was placed on the gauge anvil and the gauge foot was lowered to contact the material without compressing the material. The thickness was read to the nearest 0.0005 inches (0.5 mm). Each sample was measured three times at 4 inch intervals, and the three measurements were averaged to obtain the "gauge" for each sample.

The air porosity of each sample was determined with an RR Porosimeter, an RR Air Pressure Regulator, flow meter panel, connector tubing and gauge protector, and balloon assembly. Two inch square samples of each textile were prepared. Each sample was stretched by hand in two directions before testing. Each sample was locked into a specimen clamp and an air supply flowmeter was opened until a constant 10 inches of water reading was obtained for at least 20 seconds. After a reading on the digital flowmeter stabilizes for at least 20 seconds, this reading was recorded on a Porosity Chart. The test was repeated five times at random points on the same sample. Porosity was reported as liters per minute per square meter (LPM/M2) at the specified pressure in inches of water. The specimen clamp had a circular test area of 1,257 square millimeters, so the porosity was calculated as:

$$Porosity = LPM \times 42.5 = LPM/M2$$

Force testing for 100% extension was conducted using a universal tester machine per ASTM D412-83, specifically an Instron 4301 calibrated in accordance with SP 12.0, with a positive grip point at the edge of the jaws. The power driven machine was equipped to produce a uniform rate of jaw extension/return of 20 in/min±2 in/min (7.87 cm/min±5.08 cm/min), and had a dynamometer or load cell and suitable indicating or recording device. Samples tested were 1 inch by 6 inches (2.54 cm×15.24 cm) within a tolerance of ±1%.

Each sample was placed into the jaws of the tester. The tester was set for 2 inch (5.08 cm) benchmark. The testing cycle was set to 100% extension, 2 cycles. The test data points were recorded by the operator.

Force testing for 200% extension and 50% extension was conducted using a universal tester machine per ASTM D412-83, specifically, a Monsanto T-10 calibrated in accordance with SP 12.0, with a line contact type jaw. The power driven machine was equipped to produce a uniform rate of jaw extension/return of 20 in/min±2 in/min (7.87 cm/min±5.08 cm/min), and had a dynamometer or load cell and suitable indicating or recording device. Samples tested were 1 inch by 6 inches (2.54 cm×15.24 cm) within a tolerance of +1%. Each sample was placed into the jaws of the tester. The tester was set for 2 inch (5.08 cm) benchmark. The testing cycle was set to 200% extension, 2 cycles. The test data points were automatically recorded.

Force testing for elongation to break was conducted using a universal tester machine, specifically a Tensometer 10 calibrated in accordance with SP 12.0, with a positive grip point at the edge of the jaws. The power driven machine was equipped to produce a uniform rate of jaw extension/return of 20 in/min±2 in/min (50 cm/min±4 cm/min) and had a dynamometer or load cell and suitable indicating or recording device. Samples tested were 1 inch by 6 inches (2.54 cm×15.24 cm) within a tolerance of±1%. Each sample was placed into the jaws of the tester. The tester was set for 2 inch (5.08 cm) benchmark. The test was initiated and elongation and break force were recorded.

Force testing in a die "C" tear test was conducted using a universal tester machine, specifically a Tensometer 10 calibrated in accordance with SP 12.0, with a positive grip point at the edge of the jaws. The power driven machine was equipped to produce a uniform rate of jaw extension/return of 20 in/min±2 in/min (50 cm/min±4 cm/min) and had a dynamometer or load cell and suitable indicating or recording device. Samples tested were ¾ inch by 4 inches (½ inch width at apex) within a tolerance of±1%. Alternative samples tested were 1 inch by 6 inches (2.54 cm×× 15.24 cm) within a tolerance of±1%. Each sample was placed into the jaws of the tester. The tester was set for 2 inch (5.08 cm) benchmark. The test was initiated and tear elongation and tear force were recorded.

The table below summarizes the results of the test.

| Properties | Commercial diaper panel-construction similar to Radwanski et al. 4,879,170 | Present invention-breathable film with nonwoven fabric attached by needlepunching |
| --- | --- | --- |
| Gauge - Inches | 0.025 | 0.015 |
| Basis Weight - Lbs/SY | 0.40 | 0.194 |
| Porosity - L/MIN/M2 (Liters/Minute/Square Meter) | >>1000 | 457 |
| 100% Outgoing Power - G/LI (Grams per Linear Inch) | 257 | 191 |
| 200% Outgoing Power - G/LI | 2256 | 472 |
| 50% 2nd Outgoing relaxed power - G/LI | 64 | 58 |
| Ultimate Elongation | 275 | 300 |
| Break Force - G/LI | 3245 | 697 |
| Die C Elongation | 257 | 260 |
| Die C Force - G/LI | 1654 | 312 |
| Force Relaxation | 36% | 27% |

What is claimed is:

1. A composite comprising:
   an elastic foam film substrate having a thickness, the substrate having apertures through the thickness, each of the apertures formed from a converted foam cell; and
   a non-woven textile formed of fibers, the non-woven textile attached to the substrate by passing a portion of at least one of the fibers through at least one of the apertures.

2. The composite of claim 1 wherein the portion of at least one of the fibers is passed through the at least one of the apertures by needlepunching.

3. The composite of claim 1 wherein the elastic foam film substrate has an elongation greater than 200%.

4. The composite of claim 1 wherein the elastic foam film substrate has a high breathability and an elongation greater than 200%.

5. A composite comprising:
   a breathable elastic foam film substrate having apertures therethrough, each of the apertures formed from a converted foam cell; and
   a non-woven textile formed of strands, the textile attached to the substrate by passing a portion of at least one of the strands through at least one of the apertures.

6. The composite of claim 5 wherein the portion of the at least one of the strands is passed through the at least one of the apertures by needlepunching.

7. A composite comprising:
   an elastic foam film substrate having a thickness, the substrate having apertures through the thickness, each aperture formed from a converted foam cell, the substrate having a high breathability and an elongation greater than 200%; and
   a non-elastic, non-woven textile formed of fibers, the non-woven textile attached to the substrate by passing a portion of at least one of the fibers through one of the apertures by needlepunching.

8. A composite comprising:
   a breathable elastic foam film substrate having apertures therethrough, each aperture formed by converting a foam cell, and
   fibers attached to the foam film substrate by flocking.

9. The composite of claim 8 further comprising an adhesive attaching the fibers to the elastic foam film substrate.

10. The composite of claim 8 wherein a portion of each of the fibers is embedded in an uncured substrate, and subsequent curing of the uncured substrate attaches the fibers.

11. A composite comprising:
    an elastic foam film substrate having a thickness, the substrate having an aperture through the thickness, the aperture formed from a converted foam cell; and
    a fiber attached to the substrate by passing a portion of the fiber through the aperture.

12. The composite of claim 11 wherein the portion of the fiber is passed through the aperture by needlepunching.

13. The composite of claim 11 wherein the elastic foam film substrate has an elongation greater than 200%.

14. The composite of claim 11 wherein the elastic foam film substrate has a high breathability and an elongation greater than 200%.

* * * * *